United States Patent [19]

Zavadil

[11] Patent Number: 4,475,391

[45] Date of Patent: Oct. 9, 1984

[54] METHOD FOR MEASURING THE SPECIFIC SURFACE OF PULVERIZED MATERIALS AND APPARATUS FOR PERFORMING THE SAME

[75] Inventor: Milan Zavadil, Brno, Czechoslovakia

[73] Assignee: Vyzkumny ustav stavebnich hmot, Brno, Czechoslovakia

[21] Appl. No.: 405,929

[22] Filed: Aug. 6, 1982

[51] Int. Cl.³ .............................................. G01N 15/08
[52] U.S. Cl. ...................................... 73/432 PS; 73/38
[58] Field of Search ............................... 73/432 PS, 38

[56] References Cited

U.S. PATENT DOCUMENTS 3,416,376  12/1968  Johnson et al. ................. 73/432 PS
3,457,791  7/1969   Johnson et al. ................. 73/432 PS

FOREIGN PATENT DOCUMENTS 2025069  1/1980  United Kingdom ........... 73/432 PS
773493   10/1980 U.S.S.R. .......................... 73/432 PS

*Primary Examiner*—Gerald Goldberg
*Assistant Examiner*—Joseph W. Roskos

[57] ABSTRACT

Invention provides a method of and apparatus for measuring the specific surface of pulversized materials and includes the vibration consolidation of a sample of the material into a particular desired shape and volume, measuring the pneumatic resistance of the sample and then, using the mass density of the sample material, calculating the specific surface of the material.

5 Claims, 1 Drawing Figure

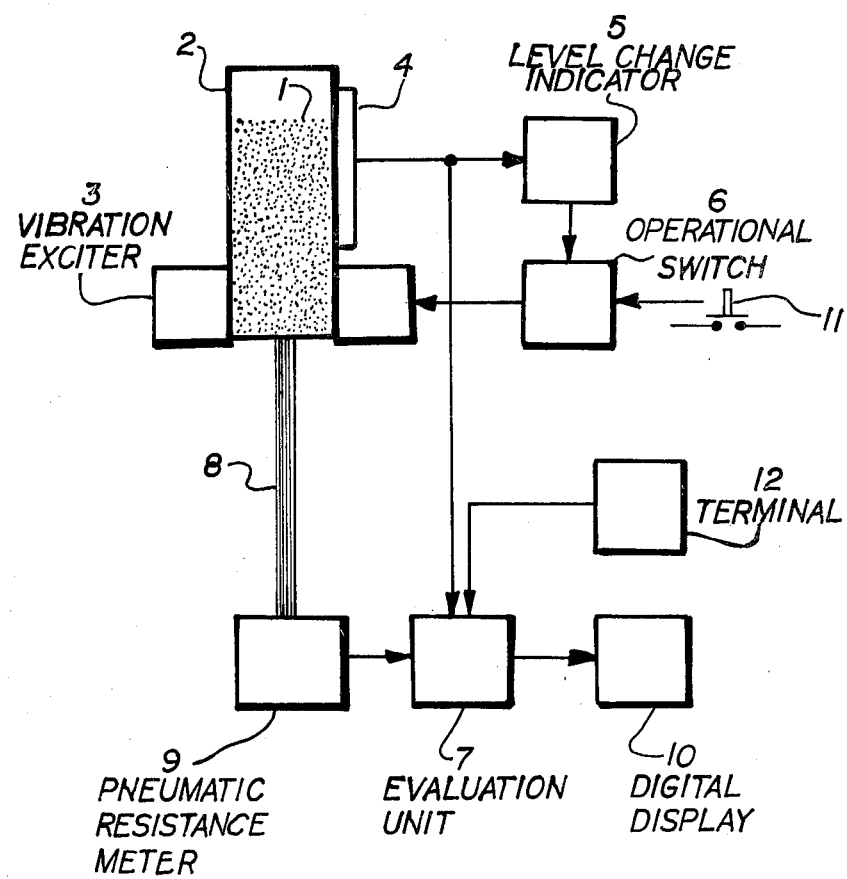

METHOD FOR MEASURING THE SPECIFIC SURFACE OF PULVERIZED MATERIALS AND APPARATUS FOR PERFORMING THE SAME

BACKGROUND OF THE INVENTION

The invention relates to a method for measuring the specific surface of pulverized materials and apparatus for performing the same.

For pulverized materials being produced and utilized in various industrial branches, the specific surface is one of the characteristic criterions of the production process and the product itself. Previously known methods for measuring this reference value are based either on the determination of the pneumatic resistance of a defined sample bed of a constant volume and mass or on the princple of a light diffraction on individual particles of the measured material.

In the first case the measurement range is limited as the compactibility of the materials being consolidated to the predetermined constant volume by means of vibration or piston compression, depends upon the particle size. For a certain sample volume setting, it is possible to measure the pneumatic resistance only in a rather small range while the measurement accuracy on the upper and lower measurement range limits decreases because of the insufficient homogenity of the sample porosity and the shape of the material sample as well. Even the time interval required for the vibration compression of the sample volume to the predetermined value varies considerably as it depends upon the material fineness. Another undesirable feature of the previously known methods is the dependence of the measuring range upon the mass density of the measured material. Samples of heavy or coarse materials are vibration consolidated to the predetermined volume value in the measuring vessel in a short time but without accomplishing the exact shape, the one being mostly of a cylindrical type. Even when pouring the given sample quantity loosely into the measuring vessel, its upper level was already below the determined volume limit. On the other hand, with very fine materials, the vibration consolidation had to carried out for a very long time which resulted in nonuniformity of the sample porosity; at times one even failed to consolidate the sample to the predetermined volume. When using the other measurement method mentioned above, its accuracy depends upon the material particle shape, and the corresponding measuring equipment is rather complicated and therefore offers lower operational reliability and the respective investment and operational costs are also high.

SUMMARY OF THE INVENTION

According to the present invention there is provided a method for measuring the specific surface of pulverized materials, the method comprising vibration consolidating a loosely poured sample into a defineable shape, subsequently measuring the sample volume and the sample pneumatic resistance, the pneumatic resistance being defined as the time interval over which a constant pressure air volume passes through the sample, and then calculating the specific surface P using the measured values in accordance with the equation $$P = \frac{K \cdot \sqrt{\epsilon^3} \cdot \sqrt{t}}{\gamma \cdot (1 - \epsilon)}$$

wherein k is an instrument constant which is to be established by calibration, t is the time interval over which the constant pressure air volume passes through the sample, $\gamma$ is the mass density of the sample material and $$\epsilon = 1 - \frac{Q}{V \cdot \gamma},$$

where Q is the mass of the sample and V is the volume of the sample.

The apparatus for performing said method comprises a measuring vessel provided with a sample volume sensing unit, the vessel being rigidly fixed to a vibration exciter for compacting the sample in the vessel, the apparatus further comprising a pneumatic resistance meter connected to a pressure air intake which opens into the measuring vessel bottom, the output of the meter being connected to the first input of an evaluation unit of which the second input is connected to a terminal for setting of the sample mass density factor, and the third input is connected to the output of the sample volume sensing unit.

The advantages of the method and apparatus include measurement of materials of any structure and any mass density, the measurement range of the apparatus being limited only by the measurement range of the sample volume sensor, which can operate either in steps or continuously. The limiting and practical stabilization of the time interval for the consolidation of samples of any material results not only in acceleration of this process operation but especially in substantial improvement of homogenity of the sample porosity and subsequent higher pneumatic resistance measurement accuracy. Combined with the evaluation unit operating in accordance with a set program, the apparatus represents a highly available unit featuring a very high measurement reproducibility and extensive application range.

DESCRIPTION OF THE DRAWINGS

The invention will be further described by way of example with reference to the accompanying drawing presenting a principal arrangement of individual elements of the apparatus.

DESCRIPTION OF THE PREFERRED EMBODIMENT

The apparatus for measurement of the specific surface of pulverized materials comprises a measuring vessel 2 provided with a sample volume sensor 4, the measuring vessel 2 being fixed to a vibration exciter 3 for compacting a sample 1 in the vessel 2. The sample volume sensor 4 may detect the established sample volume continuously or it may measure in steps, which may be managed more easily. There is a pressure air intake 8 opening into the bottom of the measuring vessel 2, the pressure air intake 8 being provided with a pneumatic resistance meter 9. The output of the pneumatic resistance meter 9 is connected to a first input of the evaluation unit 7, of which a second input is connected to a terminal 12 for setting of the mass density factor of the measured material, and a third input is connected to the output of the sample volume sensor 4. This output is also connected to the input of a level change indicator 5 the output of which is connected to a control input of an operational switch 6 of the vibration exciter 3. A digital display 10 is connected to the output of the evaluation unit 7.

The apparatus described above operates as follows: A measured material sample 1 of a given mass is loosely poured into the measuring vessel 2 and the sample mass density factor is set on the terminal 12. The starting pushbutton 11 activates the vibration exciter 3 operation switch 6 and the sample is vibration consolidated into the defined shape, preferably of a cylindrical type. In the case where the sample volume sensor 4 measures continuously, the achieved volume is recorded immediately, while in the case where the volume measuring is in steps, the vibration exciter 3 operates until the already leveled upper surface of the sample drops to the nearest lower predetermined value of the sample volume. At such moment, the signal from the sample volume sensor 4 is fed not only to the input of the evaluation unit 7 but also to the input of the volume change indicator 5 activating the operational switch 6 of the vibration exciter 3 stopping the sample consolidation. At this point the measurement of a pneumatic resistance of the sample is performed. The signal which is representative of this variable, defined as the time interval required for the passage of a constant pressure air volume through the measured sample bed, is fed to the evaluation unit 7 where the measured and set values are processed into an output signal indicative of the specific surface P of the measured material, the processing of the signal being carried out in accordance with the equation $$P = \frac{k \cdot \sqrt{\epsilon^3} \cdot \sqrt{t}}{\gamma \cdot (1 - \epsilon)}$$

where:
P is the specific surface
k is an instrument constant, i.e. a constant for the given apparatus which is to be established by calibration
t is the pneumatic resistance, the time interval required for the passage of a constant pressure air volume through the sample
$\gamma$ is the mass density of the sample
$\epsilon$ is given by equation $$\epsilon = 1 - \frac{Q}{V \cdot \gamma}$$

where
Q is the mass of the sample
V is the volume of the sample.

The measuring method is further illustrated by the following measurement record:

A sample of cement having a mass density $\gamma = 3.1$ g/cm$^3$ and a total mass Q = 110 g was loosely poured into the cylindrical measuring vessel having an internal diameter of 30 mm. The sample was vibration compacted into the cylindrical shape for 10 seconds. From the measured sample height 72.5 mm, there was calculated the sample volume V = 51.25 cm$^3$. The time interval for the passage of the constant pressure air volume through the sample was t = 44.2 sec. The instrument constant was k = 4578. Using the above presented equations, there was at first calculated the variable $$\epsilon = 1 - \frac{110}{51.25 \cdot 3.1} = 0.308$$

and substituting this figure to the other equation there was obtained the specific surface:

$$P = 4578 \cdot \frac{\sqrt{0.308^3} \cdot \sqrt{44.2}}{3.1 \cdot (1 - 0.308)} = 2422 \text{ cm}^2/\text{g}$$

The apparatus for measuring of specific surface of pulverised materials is suitable for utilization in the production of building materials like cement and powder lime, in chemical or food industry, e.g. in the manufacture of starch, cacao powder, dried milk etc., or in fuel production, e.g. for obtaining the properties of pulverised coal.

What we claim is:

1. An apparatus for measuring the specific surface of pulverized materials comprising a measuring vessel having a pressure air intake opening formed in the bottom thereof, vibration exciting means rigidly connected to said measuring vessel, sample volume sensing means coupled to said measuring vessel for sensing the volume of the sample material held therein, pneumatic resistance measuring means coupled to said pressure air intake opening in said measuring vessel for measuring the pneumatic resistance of the sample material, and an evaluation unit having a first input coupled to said pneumatic resistance measuring means for receiving the value of pneumatic resistance, a second input coupled to a terminal means for inputting the mass density factor of the sample material and a third input coupled to said sample volume sensing means for receiving the volume of the sample material, said evaluation unit providing at an output thereof the specific surface of the sample material in accordance with the equation:

$$P = \frac{k \cdot \sqrt{\epsilon^3} \cdot \sqrt{t}}{\gamma \cdot (1 - \epsilon)}$$

where:
P is the specific surface,
k is an instrument constant,
t is the pneumatic resistance, the measured time interval for the passage of a constant pressure air volume through the sample,
$\gamma$ is the sample mass density, and
$\epsilon$ is given by the equation:

$$\epsilon = 1 - \frac{Q}{V \cdot \gamma}$$

where:
Q is the mass of the sample, and
V is the volume of the sample.

2. The apparatus according to claim 1, characterized in that the apparatus further comprises a digital display coupled to the output of the evaluation unit.

3. The apparatus according to claim 1 or 2, characterized in that the apparatus further comprises level change indicating means also coupled to the output of said sample volume sensing means, and operation switching means coupled to the vibration exciting means for the control thereof, said operation switching means having a control input coupled to an output of said level change indicating means.

4. In a method of measuring the specific surface of pulverized material, comprising a preparation of a sample bed and applying a fluid pressure to the sample and measuring the resistance of the prepared sample bed to the flow of the fluid therethrough, an improvement comprising vibration consolidating the loosely poured material of known mass into a geometrically defined shape, measuring the sample volume and its pneumatic resistance, the pneumatic resistance being defined as the time interval for the passage of a constant pressure air volume through the sample, and determining the specific surface P using the equation:

$$P = \frac{K \cdot \sqrt{\epsilon^3} \cdot \sqrt{t}}{\gamma \cdot (1 - \epsilon)}$$

where:
P is the specific surface,
k is an instrument constant,
t is the pneumatic resistance, the measured time interval for the passage of a constant pressure air volume through the sample,
γ is the sample mass density, and
ε is given by the equation:

$$\epsilon = 1 - \frac{Q}{V \cdot \gamma}$$

where:
Q is the mass of the sample, and
V is the volume of the sample.

5. The method according to claim 4, comprising a further vibration consolidation of the sample having already a geometrically defined shape until the nearest lower value of reading the sample volume is achieved.

* * * * *